United States Patent [19]
Urtti et al.

[11] Patent Number: 5,518,737
[45] Date of Patent: May 21, 1996

[54] PERORAL DRUG DELIVERY SYSTEM

[75] Inventors: Arto O. Urtti, Kuopio; Marja R. Sutinen, Siilinjärvi; Timo P. Paronen, Kuopio, all of Finland

[73] Assignee: Orion-yhtymä Oy, Espoo, Finland

[21] Appl. No.: 211,292

[22] PCT Filed: Oct. 15, 1992

[86] PCT No.: PCT/FI92/00274

§ 371 Date: May 5, 1994

§ 102(e) Date: May 5, 1994

[87] PCT Pub. No.: WO93/07858

PCT Pub. Date: Apr. 29, 1993

[30]    Foreign Application Priority Data

Oct. 16, 1991 [GB]  United Kingdom ............ 9121964
Nov. 4, 1991 [GB]  United Kingdom ............ 9123372

[51] Int. Cl.⁶ ............................................. A61K 9/22
[52] U.S. Cl. .................. 424/473; 424/469; 424/481; 424/485; 424/489; 424/490; 424/496
[58] Field of Search ........................ 424/473, 469, 424/481, 485, 489, 490, 496

[56]                 References Cited

U.S. PATENT DOCUMENTS

| | | | |
|---|---|---|---|
| 4,656,027 | 4/1987 | Sjöqvist | 424/495 |
| 4,756,710 | 7/1988 | Bondi | 424/449 |
| 4,781,924 | 11/1988 | Lee et al. | 424/449 |
| 4,795,644 | 1/1989 | Zentner | 424/468 |
| 4,968,505 | 11/1990 | Okada et al. | 424/400 |

FOREIGN PATENT DOCUMENTS

| | | |
|---|---|---|
| 0069097 | 1/1983 | European Pat. Off. |
| 0281204 | 7/1988 | European Pat. Off. |
| 0350246 | 1/1990 | European Pat. Off. |
| 2223047 | 10/1974 | France |
| 2635460 | 8/1990 | France |

OTHER PUBLICATIONS

Hawley's Condensed Chemical Dictionary, 12 ed, Richard J. Lewis, Sr, 1993, p. 455.

"Elementary Osmotic Pump", Felix Theeuwes, Journal of Pharmaceutical Sciences, vol. 64, No. 12, Dec. 1975, pp. 1987–1991.

Primary Examiner—D. Gabrielle Phelan
Attorney, Agent, or Firm—Burns, Doane, Swecker & Mathis

[57]                    ABSTRACT

This invention describes a device for peroral administration of a therapeutic agent which is capable of existing in an unionized therapeutically active form. The device comprises a reservoir comprising the therapeutic agent in ionized form, which reservoir has a wall permeable to un-ionized material and impermeable to ionized material; and a solid material which upon uptake of water is converted to a buffer; the solid material having, on uptake of water, a pH which determines the rate of permeation of the therapeutic agent in un-ionized form through the reservoir wall. The device enables the release of the therapeutic agent to be controlled by the pH of the buffer and, if desired, the composition of the reservoir walls. The composition of the surrounding aqueous medium does not affect the rate of release.

16 Claims, 15 Drawing Sheets

PERORAL DRUG DELIVERY SYSTEM

FIELD

This application is a 371 of PCT/FI92/00274 filed Oct. 15, 1992.

This invention is related to peroral drug delivery of weak electrolytes. Specifically the invention describes a pharmaceutical product with a plurality of ingredients in which drug release can be modified over a wide range independently of the surrounding pH, osmotic pressure, and ionic strength.

BACKGROUND

Most drugs that are in clinical use are either weak bases, weak acids or their salts. Due to their pH-dependent solubility and dissociation, weak bases and weak acids have pH-dependent rates of drug dissolution. Substantial dissolution rate variations may become a problem in peroral drug delivery, if the compound has poor solubility in its un-ionized state and much higher solubility in its ionized state. pH varies considerably in the different parts of the gastrointestinal tract (between 2 and 7) and, thus, dissolution rate may also change during the transit of the dosage form in the gastrointestinal tract.

The pH may also vary in the stomach of an individual at different times relative to feeding. Also, the transit of the dosage form in the gastrointestinal tract has considerable interindividual and intraindividual variation. For the reasons mentioned above weak electrolytes may show dissolution rate controlled variations in their rates of absorption and consequently in their therapeutic activity.

Attempts to overcome the problem of pH-dependent variations in drug delivery include the development of osmotic pumps and buffered tablets (DE 2414868 and Theeuwes F., J. Pharm. Sci. 64: 1987, 1975). The osmotic devices are based on the osmotic influx of water from the surroundings into the device with high inner osmoticity. Water influx pushes drug solution from the dosage form through an orifice. Drug release from the osmotic devices is constant for a considerable period and it is not dependent on the surrounding pH. A disadvantage of these devices is that they are fairly complicated to manufacture and only drugs with high water-solubility can be used. In addition osmotic pumps have been known to adhere to the walls of the gastrointestinal tract causing severe local irritation.

In buffered tablets (DE 2414868) the drug crystals and solid-state buffer are mixed together so that during dissolution the microenvironmental pH in a tablet can be adjusted to be more favourable from the standpoint of drug dissolution. In these dosage forms drug release is controlled by microenvironmental pH. When the degree of drug ionization (and solubility) is increased with the buffer its dissolution rate is increased (DE 2414868). However, it should be remembered that the microenvironmental pH on the surface of drug crystal is in direct contact with bulk pH and bulk buffers. Consequently, it is affected by the surrounding bulk pH.

An attempt to overcome the problems relating to the storage in transdermal drug preparation of drugs which are weak acids or weak bases is described in U.S. Pat. No. 4,781,924. This patent discloses a transdermal system where the therapeutic agent, which in its active form is either an acid or a base, during the storage of the preparation exists in an inactive form, preferably a salt not being able to migrate out from the reservoir containing said therapeutical agent. The transdermal preparation further contains an activating agent, an acid or a base, which exists in an anhydrous form during storage. When the transdermal preparation is placed upon the skin, moisture from the human body diffuses into the system and converts the activating agent to the corresponding acid or base solution which further converts the salt form of the therapeutic agent to the corresponding free acid or free base.

The U.S. Patent cited above presents only the initial activation of the drug release. No ways to control the rate of drug release from the system have been demonstrated. Neither is there any suggestion that any similar phenomenon could or would work in oral preparations.

The present invention provides a controlled release device for peroral delivery of a therapeutic agent capable of existing in an un-ionized therapeutically active form, the device comprising:

a reservoir comprising the therapeutic agent in ionized form, which reservoir has a wall permeable to un-ionized material and impermeable to ionized material; and a solid material which upon uptake of water is converted to a buffer;

the solid material having, on uptake of water, a pH which determines the rate of permeation of the therapeutic agent in unionized form through the reservoir wall.

Release of the un-ionized therapeutic agent from the device described herein is dependent only on the design and composition of the device, not on the properties of the surrounding dissolution medium. The reservoir wall acts as a semi-permeable membrane which is impermeable to ionized material and permeable to un-ionized material. With the device it is possible to control the intensity of the initial release burst and also to avoid the burst completely. The described device enables the control over a wide range of the steady-state drug release after the initial lag or burst without even changing the composition of the semi-permeable membrane. Changing or modifying the composition of this membrane offers further possibilities to modify the release behaviour.

Figure 1A:
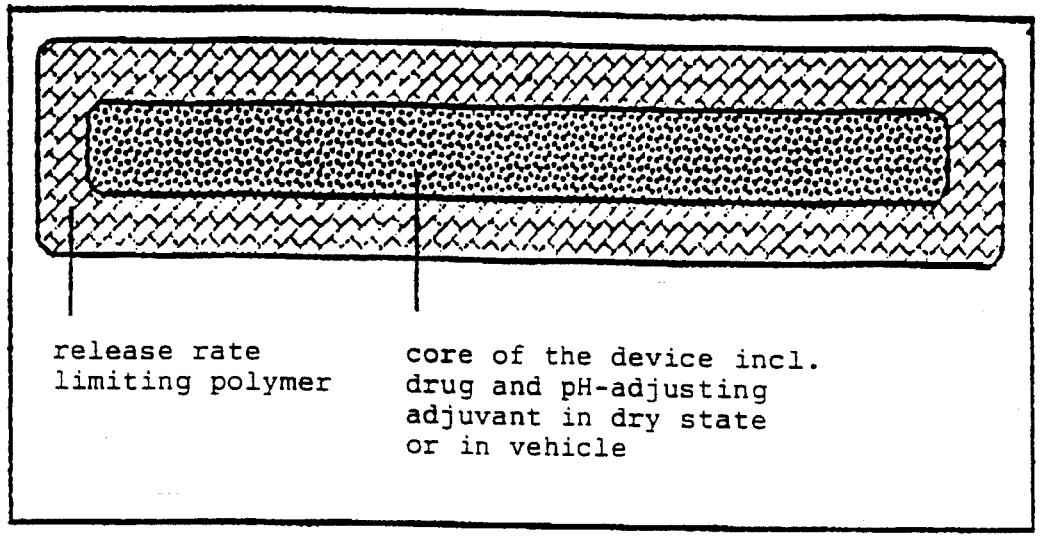
FIG. 1: Shows embodiments of the invention in which the reservoir comprises a single core.
Figure 1B:
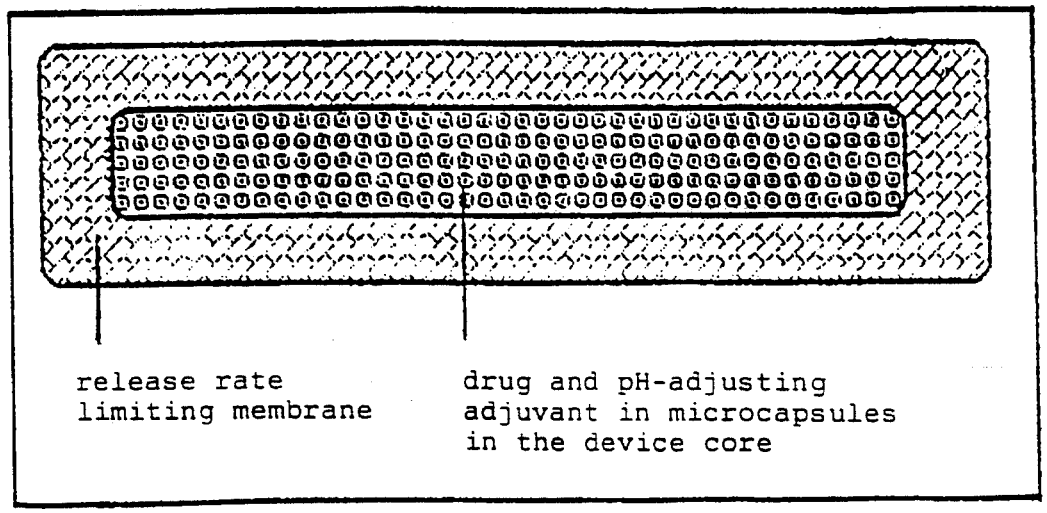
Figure 2:
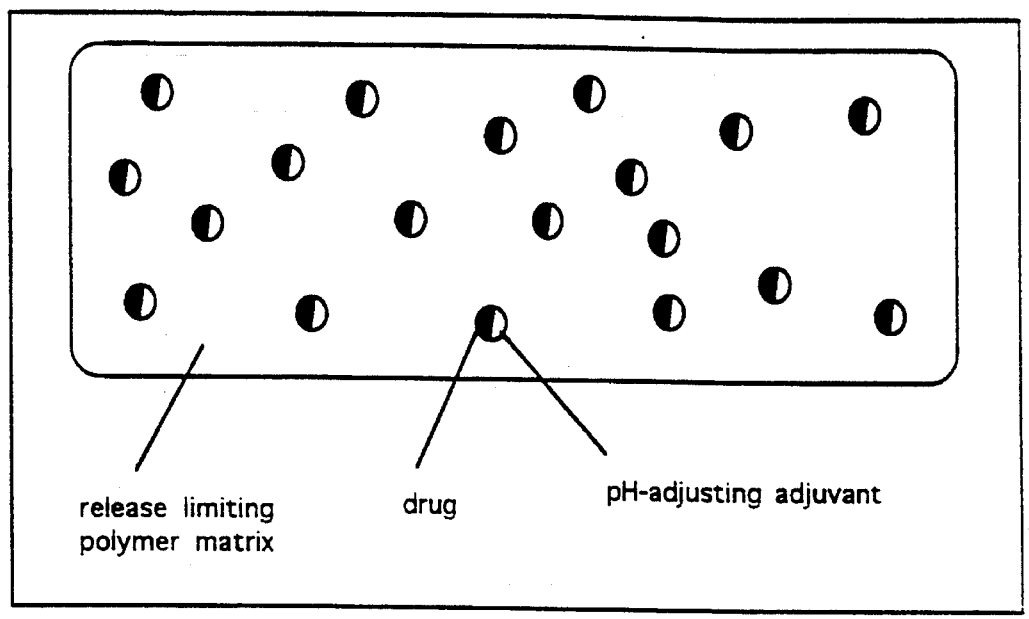
FIG. 2: Shows an embodiment of the invention in which the reservoir comprises a plurality of individual cores.
Figure 3:
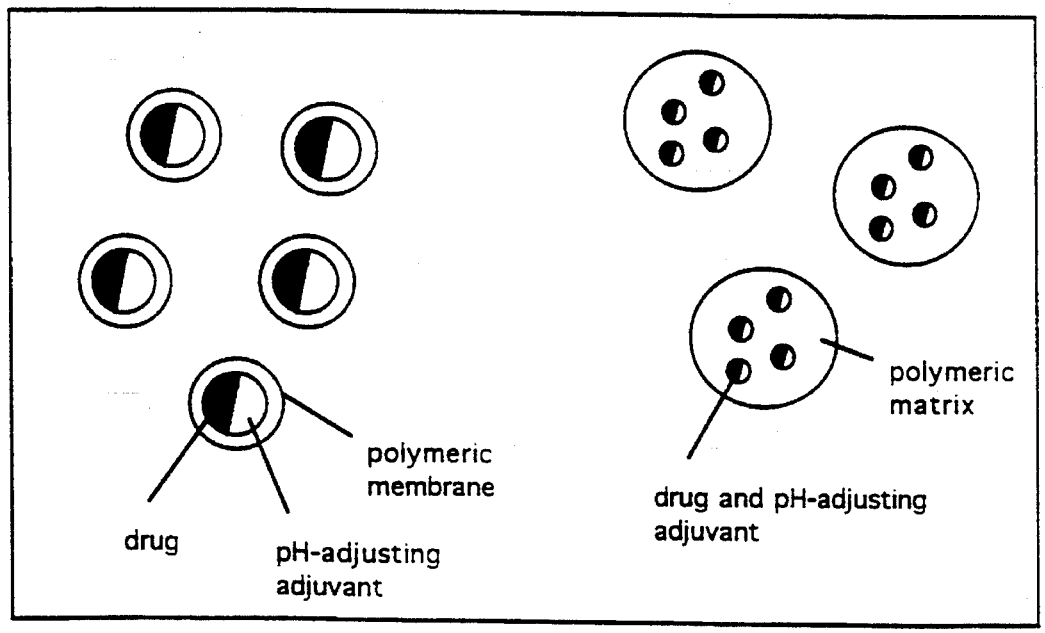
FIG. 3: Shows a further embodiment of the invention in which the reservoir comprises a plurality of individual cores.

The device comprises a drug reservoir containing a solid material, hereinafter referred to as "buffer precursor", which on uptake of water is converted to a buffer. This buffer, together with the semi-permeable membrane, controls the release rate of the drug. The reservoir may comprise a single macroscopic core, which is surrounded by the membrane (FIG. 1). Alternatively there may be numerous small cores each containing the drug and appropriate buffer precursor. These small cores may be located in a polymer matrix (FIG. 2) or they may be in microspheres or microcapsules, with each microsphere containing one or more cores (FIG. 3). The microspheres may be administered e.g. in gelatin capsules.

Each macroscopic or individual, small core contains a drug which during storage is in its solid-state form (a salt, weak acid or weak base). The device may be used for the controlled release of a variety of drugs. The drug should be capable of existing in ionized form and in a therapeutically active un-ionized form. In particular the device may be used with any acidic or basic drug which can exist in ionized form if its un-ionized form has adequate permeability in the reservoir wall. Therapeutic compounds which may be delivered using this system include $\beta$-adrenoceptor blocking agents, analgesics, anti-arrhythmic agents, antibacterial agents, anticonvulsants, antidepressants, antihistamines, antihypertensives, antipsychotics, antiulcer drugs, bronchodilators, diuretics, hypoglycaemic agents, parasympathomimetics, sympathomimetics and vasodilators. The device is particularly useful for the administration of drugs over a sustained period of time, or drugs whose release rate is difficult to control using other methods e.g. an osmotic device because the drug does not have a sufficiently high water solubility.

The core may also contain a vehicle that does not affect the release of the drug (e.g. Silastic Adhesive or other semi-solid vehicle in which the drug is placed). One or more other suitable adjuvants may be present.

Figure 4:
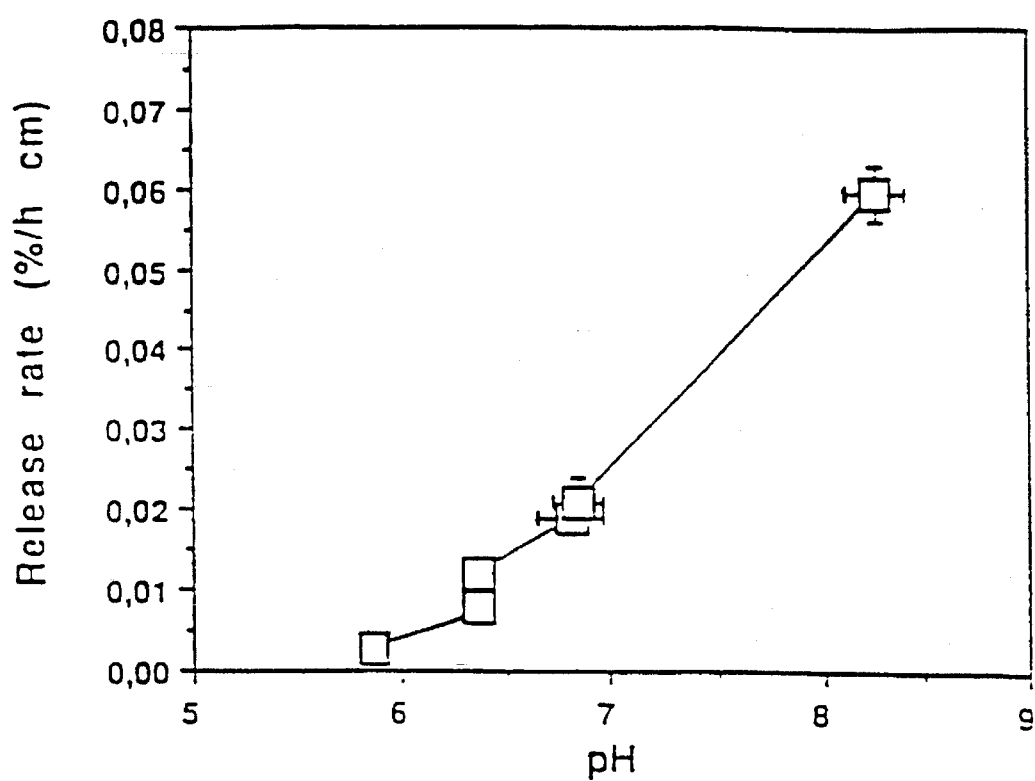
FIG. 4: Shows the effect of core pH on the release rate of a drug.

The core also contains a buffer precursor which forms a pH-adjusting buffer that both triggers and controls the rate of drug release upon the entrance of water in the core. The release-controlling buffering agent affects the pH of the core, when water enters the core after the device enters the digestive tract. Possible buffering agents include mon-, di-, and tribasic salts of phosphates, Tris-buffer, carbonates, bicarbonates, acetates, sulfates, sulfites, borates, citrates, nitrates, etc. When the resulting pH in the core of the device is increased by the buffering agent, the fraction of un-ionized weak base drug in the core is increased and drug penetration through the membrane is increased (FIG. 4). In the case of weak acids the opposite is true: decreased pH of the buffer improves the drug permeation from the device core across the membrane. This release controlling technology is applicable to all weak acids and weak bases whose un-ionized form has adequate permeability in the rate-controlling membrane.

The rate-limiting membrane of the device is a suitable semipermeable membrane (i.e., is a rate-limiting elastomeric polymeric membrane). This means that the membrane does not allow penetration of the ionized salts from the device core across the membrane nor does it let buffers from the dissolution medium penetrate into the device core. However, the membrane permits adequate penetration of water to the core of the device and it allows the penetration of un-ionized base or acid from the core across the membrane. Ionized drug and adjuvants e.g. buffers do not diffuse from the device. The pH in the device core and, subsequently, the degree of ionization of the drug determine how much drug partitions from the core to the rate-limiting membrane.

Thus, this device is a partition-controlled system which differentiates between the ionized and un-ionized drug. The semi-permeable nature of the membrane makes it very difficult for any buffer material in the dissolution medium to penetrate to the inner core of the device. Consequently, the pH in the device core is maintained nearly constant regardless of any large pH variations outside.

Conveniently the membrane comprises a polymer. Suitable polymers to form the rate-limiting elastomeric polymeric membrane are hydrophobic or hydrophilic and have enough free volume between polymeric chains to allow diffusion of water, preferably slowly, but not diffusion of larger charged species. For example elastomer-type polymers fulfill these criteria. Suitable polymers include silicones, polyisobutylene, polyhydroxyethyl methacrylate, silicone-polyethyleneoxide copolymers, styrene-butadiene copolymers etc. The rate limiting membranes can be prepared by solvent casting, compression molding, emulsion vulcanization, emulsion and suspension polymerization and other known methods.

Rate of water influx through the membrane can be accelerated by using a more hydrophilic membrane or by adding hydrophilic adjuvants to the membrane (e.g. mannitol, polyethylene glycols, glycerol, sucrose, sodium chloride, potassium chloride etc.). Also the release rate of hydrophilic drugs can be increased by making the rate-limiting membrane more hydrophilic. Conversely the rate of water influx through the membrane can be decelerated by using a more hydrophobic membrane or by adding hydrophobic adjuvants to the membrane.

Figure 5:
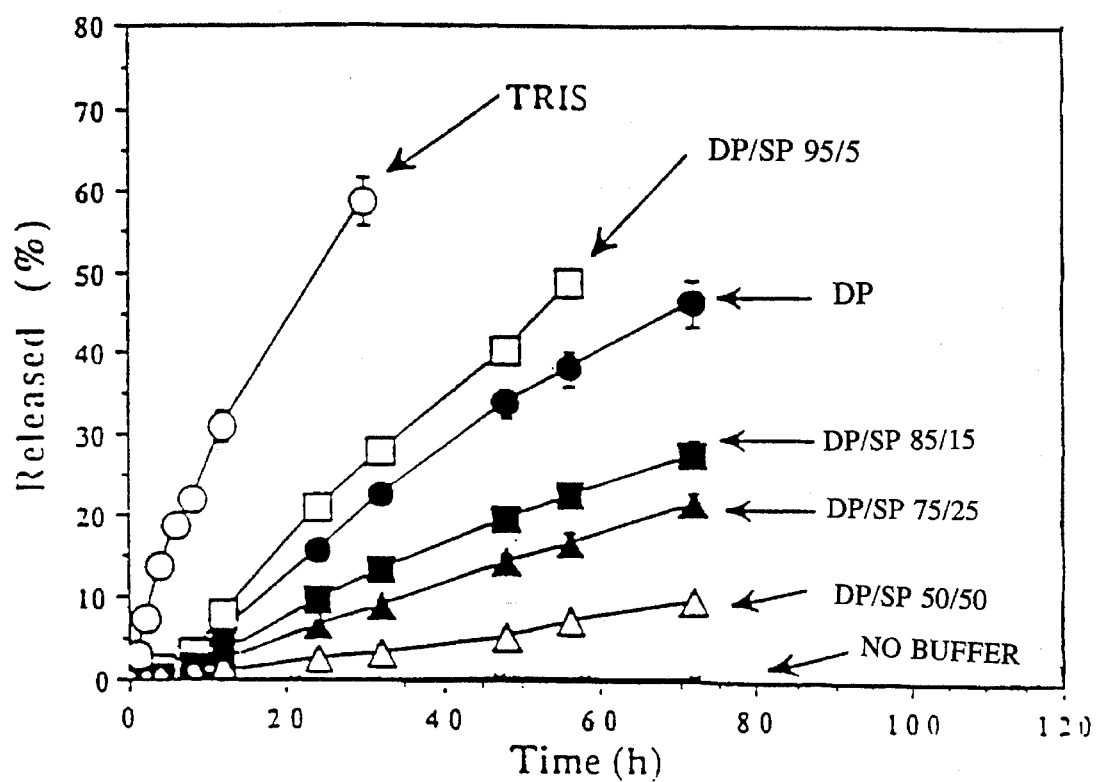
FIG. 5: Shows the effect of different buffers on the release rate.

In its salt form the drug does not penetrate into the membrane during storage, but as free base or acid it may saturate the rate-limiting membrane during the shelf-life. After ingestion, trace amounts of water penetrate through the membrane into the device core, where it dissolves part of the drug and buffer precursor. An un-ionized portion of the dissolved drug penetrates through the rate-limiting membrane. During the initial stage the rate of drug release slowly increases until drug concentration in the membrane reaches a steady-state level. Consequently, a time delay before steady drug release rate is observed (FIG. 5).

In the case of free acid or base, membrane saturation during storage results in an initial burst of drug being released on administration. After the initial rapid release a steady-state is achieved in the membrane and drug release is determined thereafter by the pH-control in the core.

The magnitude of the burst or delay in the drug release can also be modified by preloading the rate-limiting membrane. The loading can be done by incubating the polymer membrane in a drug solution. The resulting drug concentration in the membrane is determined by the polymer/solution partition coefficient of the drug and by the drug concentration in the solution. By changing the pH, temperature, and drug concentration in the incubation solution different loading levels of the drug in the membrane are achieved.

The maximum drug concentration that can be attained in the polymer by incubation method is set by the solubility of the drug in the polymer.

The device may be produced by first producing the core or cores and placing them in contact with the membrane. The drug and adjuvant or adjuvants can be simply mixed as a homogeneous powder mixture or spray dried, or lyophilized together and placed using a suitable method as the core(s) of the device. The core or cores may be encapsulated between polymer membranes or be dispersed in a polymer. Matrices and membranes, which are typically in the form of sheets which may be flat or shaped, may be produced by e.g. compression molding or solvent casting. Disperse systems may be produced by suspension or emulsion polymerization or film coating procedures.

The reservoir wall which acts as a membrane is preferably in direct contact with the contents of the reservoir. The membrane may surround the reservoir wholly or only partially. Conveniently the reservoir is substantially completely surrounded by the membrane, but it may in some instances be preferable to surround a part of the reservoir, when it is a single macroscopic core, with an impermeable material.

The following examples illustrate the invention.

EXAMPLES

1. Single Core Device

(a) Effect of the Device Core Composition

Silastic (registered trade mark) Q7-4840 A/B Medical Grade Liquid Silicone Rubber (Dow Chemical Corning, Midland, Mich., U.S.A.) was used to form membranes. It consists of semisolid components, A and B, which are mixed in equal portions. Upon compressing at 60° C. for 1 hour the mixture is vulcanized (crosslinks) via platinum catalyst addition (hydrosilylation) reaction. The thickness of the membranes was 150 µm. Solid propranolol hydrochloride (2 mg) was placed without or with pH-adjusting additives (sodium phosphate/disodium phosphate in different proportions, Tris buffer) (2 mg) on a cut piece of silicone membrane. Another silicone membrane was glued on the former so that the drug and, if present, adjuvant were encapsulated inside two membranes. The pH adjusting agents were used to produce devices each of which had a different core pH, varying from 5.8 to 8.25.

Propranolol release from the devices was studied in vitro at pH 7.4 in phosphate buffer from one side of the device in side-by-side diffusion cell. The exposed drug releasing surface was 0.7 cm$^2$. The released propranolol was analysed using reverse phase HPLC at 254 nm. Similar devices were also immersed in phosphate buffer for 24, 48 and 72 hour and the pH of the core of the device was determined using a microelectrode.

The pH in the core of each device remained essentially constant during the test period. FIG. 4 shows how the release rate of propranolol from each device depends on the pH of the core. The range of release rates is 700-fold between the lowest and the highest rates of release.

FIG. 5 shows how the amount of propranolol released from each device varied with time for devices containing different buffers. From FIG. 5 it is evident that there is direct relationship between the core pH and the release of propranolol. Any desired rate of propranolol release in the range shown in FIG. 5 can be attained by choosing an appropriate combination of buffer adjuvants in the core of the device. The range can be changed by affecting the core buffer, membrane thickness, and surface area of the membrane.

Figure 6:
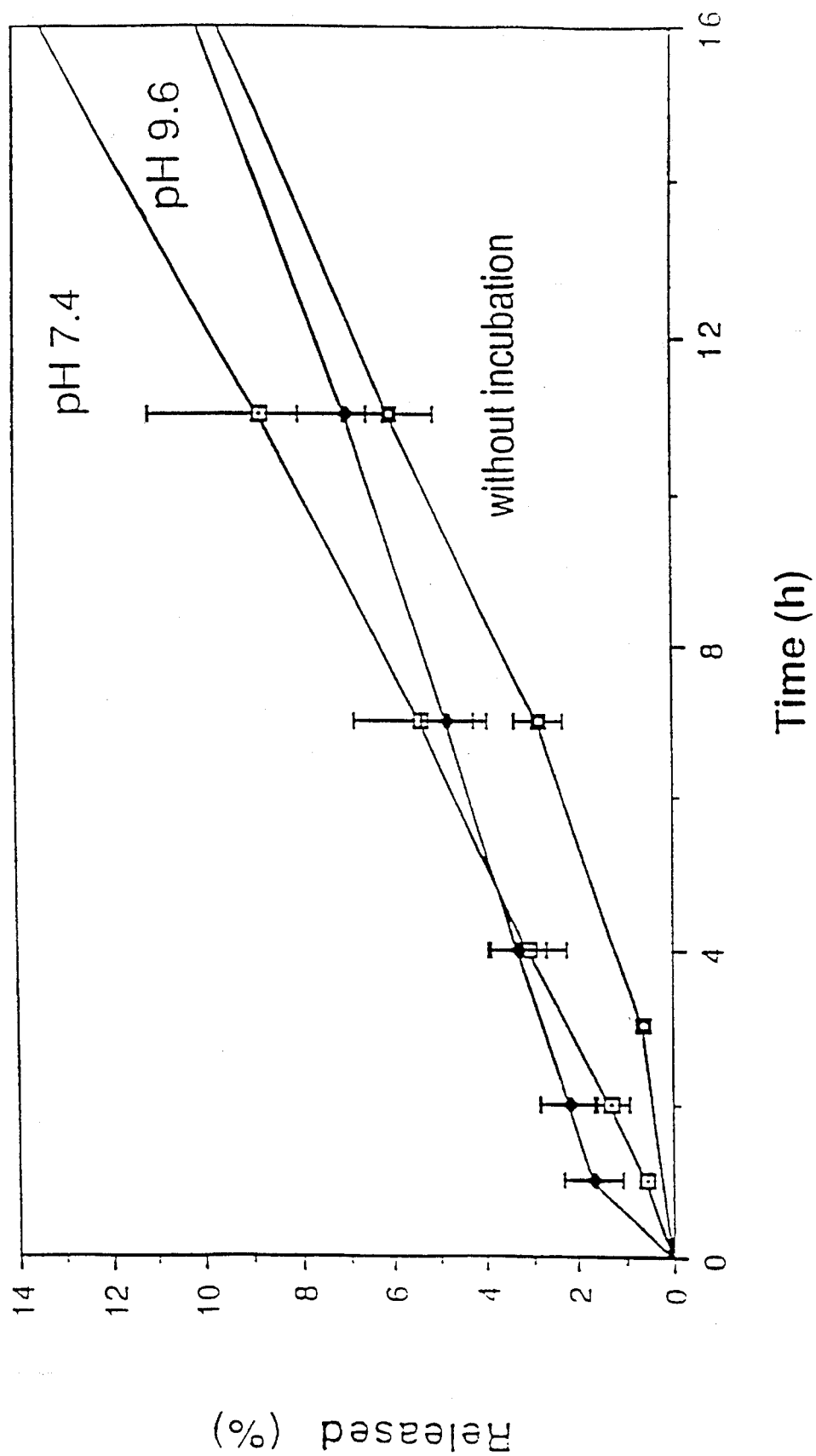
FIG. 6: Shows the effect on release rate of incubating the membrane at different pH before preparing the device.

If the pieces of the membranes are incubated at pH 7.4 or pH 9.0 propranolol hydrochloride solutions prior to device preparation it is possible to avoid the initial lag time before the steady drug release. The effect on drug release by such incubation is shown in FIG. 6.

(b) Effect of the Dissolution Medium

Silicone reservoir devices were prepared and tested as described above. Two milligrams of propranolol hydrochloride and disodium phosphate were used in the devices. The effect of pH, ionic strength and osmolality of dissolution medium on the drug release was tested in buffer solutions with four different pHs (1.6, 4.6, 7.3, 9.4), osmotic pressures (138, 295, 550 or 950 mOsm) and different ionic strengths (0.15 or 0.30M). pH 1.6 buffer solution consisted of HCl an KCl, pH 4.6 acetic acid (0.1M) and sodium acetate (0.1M), and pH 7.3 buffer was a mixture of sodium phosphate and disodium phosphate. pH 9.4 buffer solution was made of 0.1M disodium carbonate adjusting the pH of solution with 0.3M HCl. The ionic strength of the solutions was adjusted with sodium chloride. The osmotic pressures (mOsm) of the dissolution media were adjusted with sucrose and they were determined by an osmometer (Osmostat OM-6020, Daiichi Kagaku, Kyoto, Japan).

Solubility of propranolol hydrochloride in buffer solutions at 34° C. was investigated by shaking propranolol hydrochloride suspension in the solvent. After equilibration, the saturated solutions were filtered and the concentration of propranolol in the filtrates was assayed by HPLC as described above. The dissolution rate of propranolol hydrochloride in the buffer solutions (pH 1.6, 4.6, 7.3 or 9.4; 550 mOsm; $\mu$=0.3) was determined by a rotating disc method in a Sotax Dissolution Tester (AT6, Sotax, Switzerland) at 34° C. For the test, propranolol hydrochloride discs of 150 mg were prepared using a hydraulic press with punches of 13 mm in diameter. A compression pressure was about $10^3$ MPa and it was maintained for 10 minutes. In the test, the rotation speed of the discs was 100 rpm, and the volume of dissolution medium 750 ml. At predetermined intervals the concentration of propranolol in the dissolution medium was determined using RP-HPLC. The dissolution rate was calculated as the slope of the linear portion of the cumulative amount of dissolved vs time plot. Each experiment was repeated five times.

Figure 7:
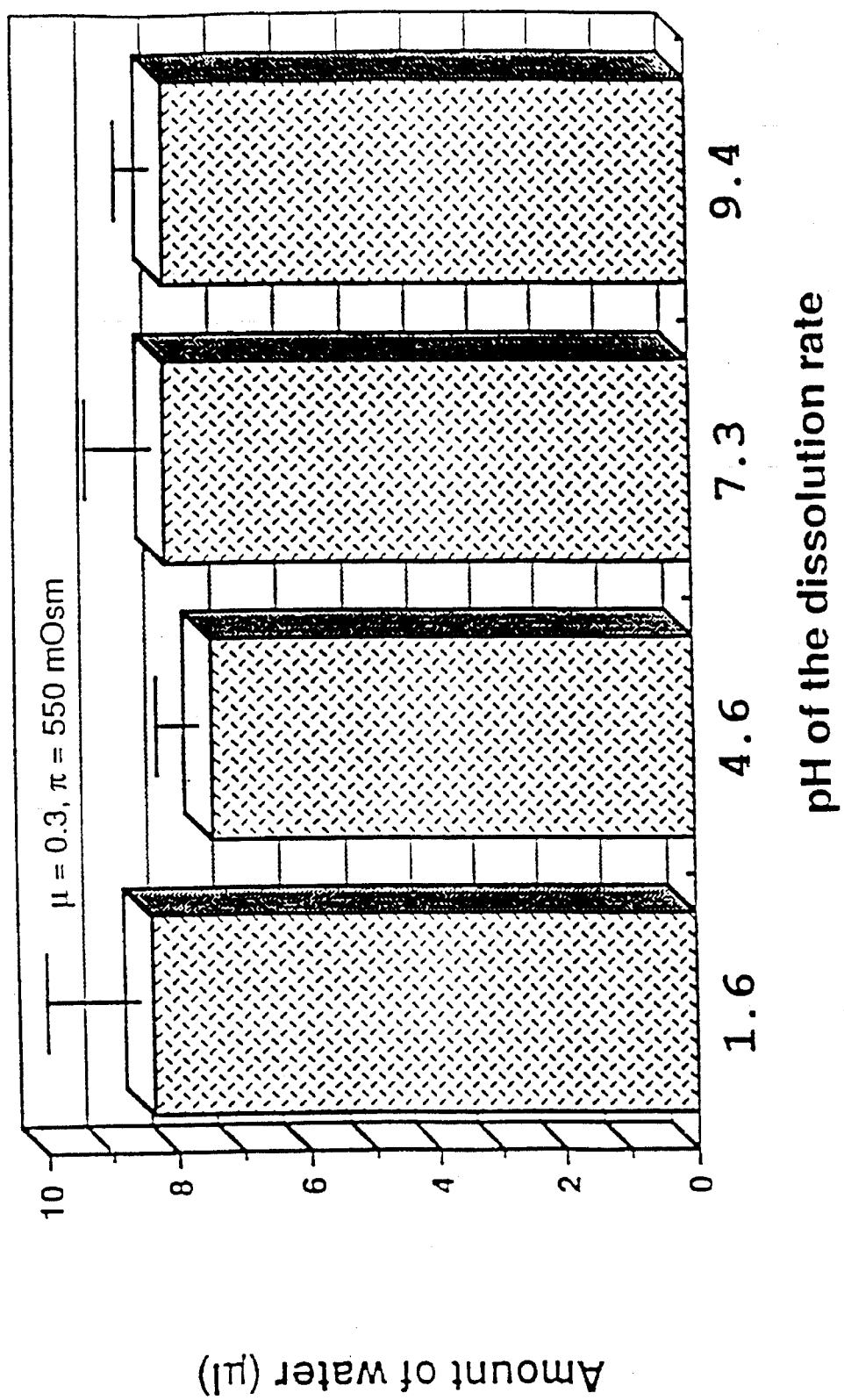
FIG. 7: Shows the amount of water absorbed into devices when the devices are placed in dissolution media of different pH.
Figure 8:
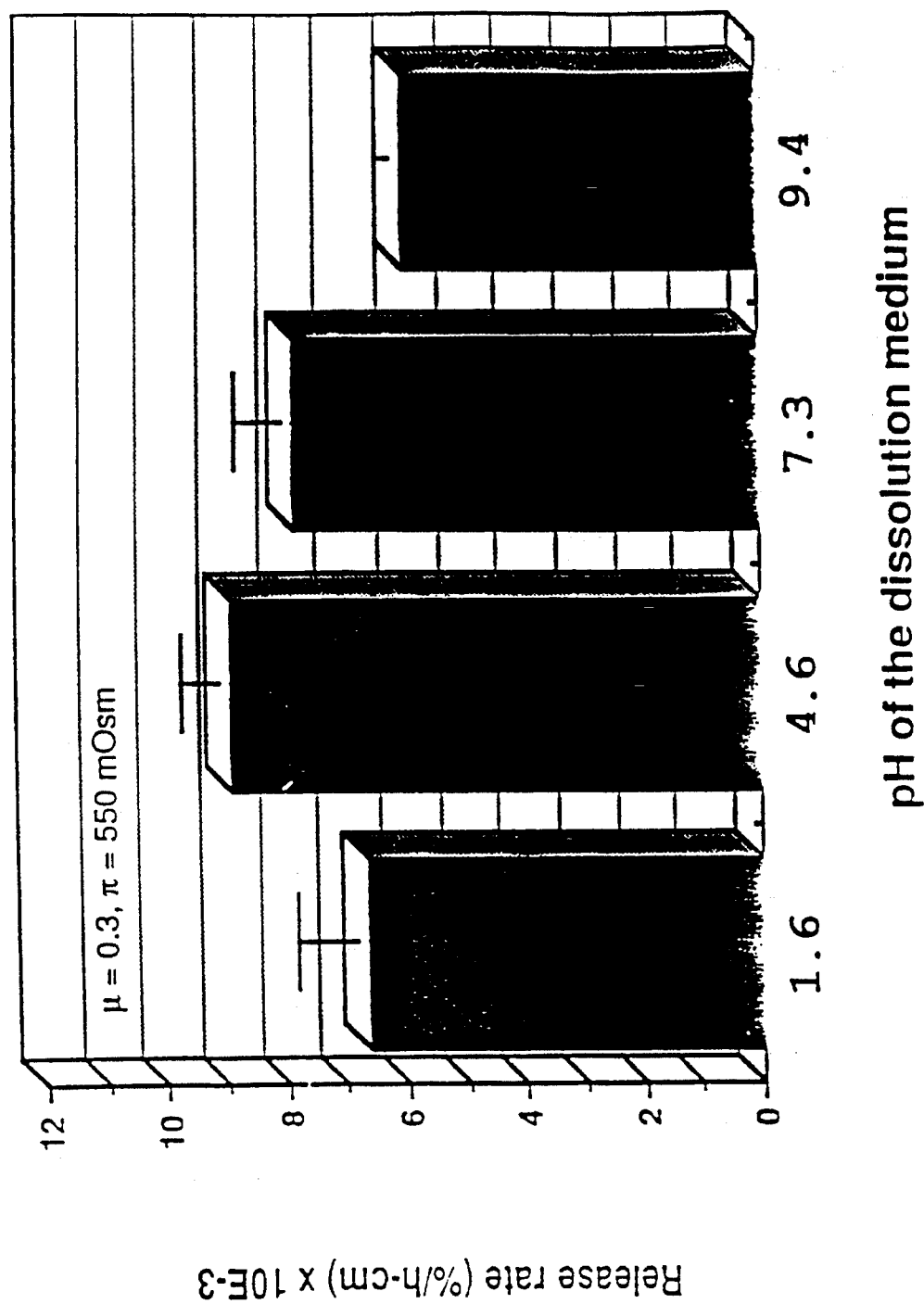
FIG. 8: Shows the drug release rate from devices in dissolution media at different pH.
Figure 9:
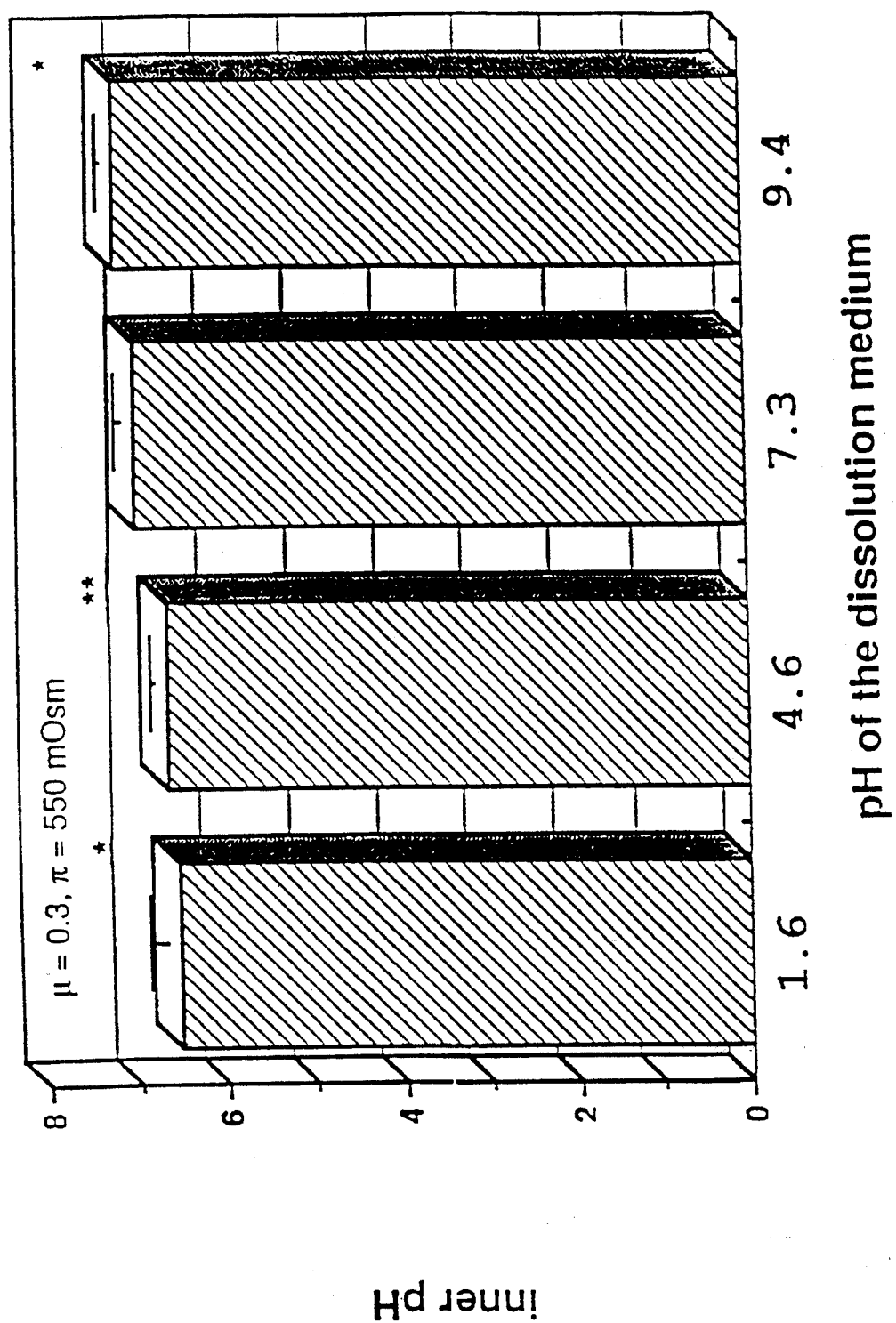
FIG. 9: Shows that the pH of the reservoir inside the device remains substantially unaffected by the pH of the dissolution medium surrounding the device.

The average amount of water absorbed into the device cores during the test was 6–10 µl and it was not affected by the pH of the dissolution medium. This can be seen from FIG. 7. The amount of water absorbed into the device core was adequate to dissolve the drug and phosphate. This was seen as propranolol release from the device. Drug release rates for the different dissolution media pH are depicted graphically in FIG. 8. It can be seen that release rate is practically unaffected by the surrounding pH. Likewise the inner pH in the dosage form was affected minimally (i.e. 0.6 units) even though the pH in the dissolution medium was changed from pH 1.6 to 9.4. The inner pH values at the various dissolution media pH are shown in FIG. 9.

The inner pH was so independent of the surrounding pH because of the buffering effect of the phosphate and barrier properties of the silicone wall. The silicone wall prevents free diffusion of the buffer from the device as well as preventing free diffusion of buffers from the dissolution medium into the device.

Figure 10:
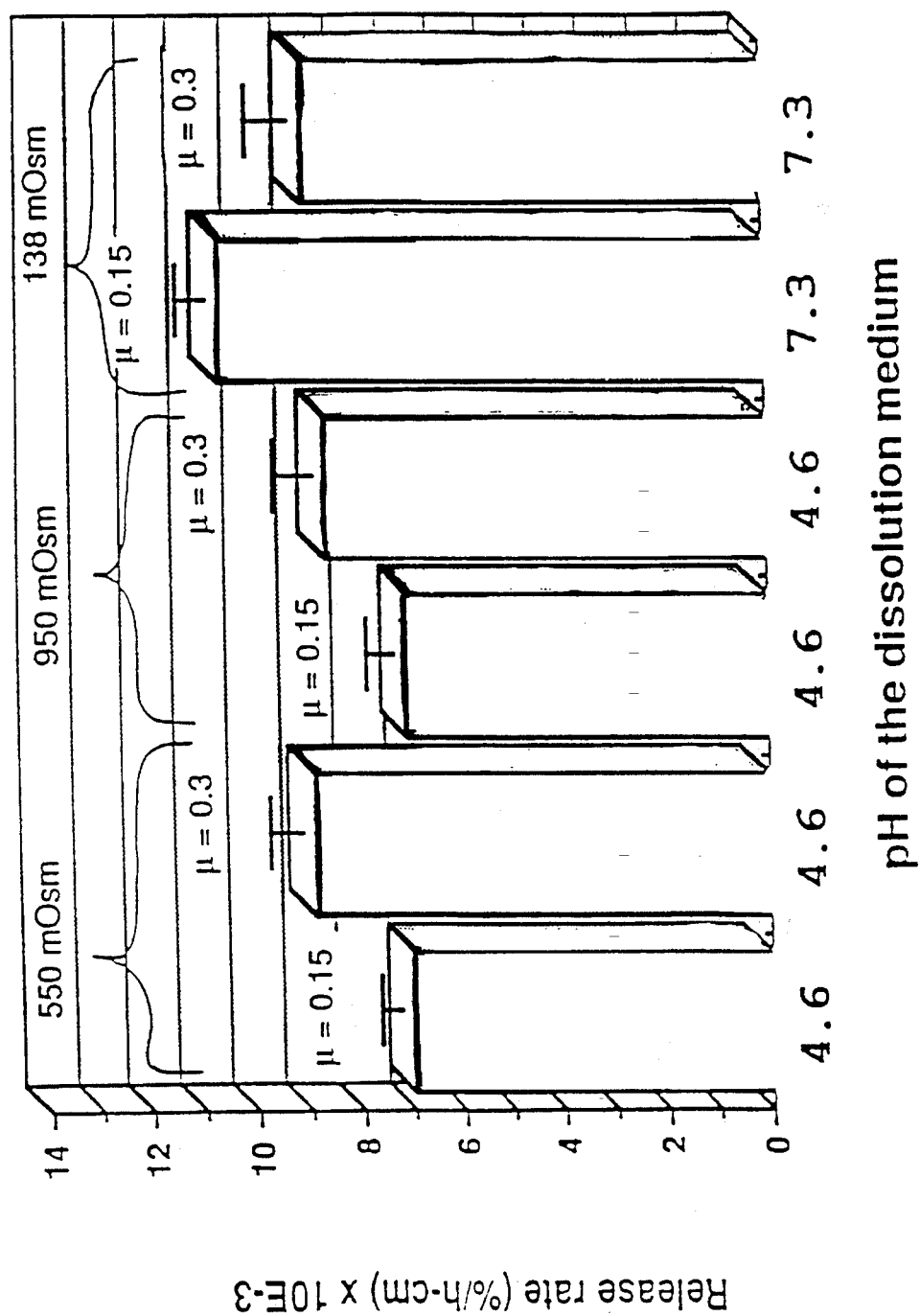
FIG. 10: Shows how the ionic strength of the dissolution medium affects the release rate.

The change in the ionic strength of dissolution medium from 0.15 to 0.3 at pH 4.6 and at pH 7.3 did not affect the imbibition of water into the devices. At pH 4.6, the amounts of water in the core at the end of the test were 7.4±0.8 µl and 7.4±0.6 µl with µ=0.15 and µ=0.3, respectively. The corresponding values at pH 7.3 were 8.5±0.5 µl and 7.4±0.5 µl. Also, the release profile and rate of propranolol release from the silicone reservoir devices were independent of the ionic strength of the dissolution medium (FIG. 10).

Figure 11:
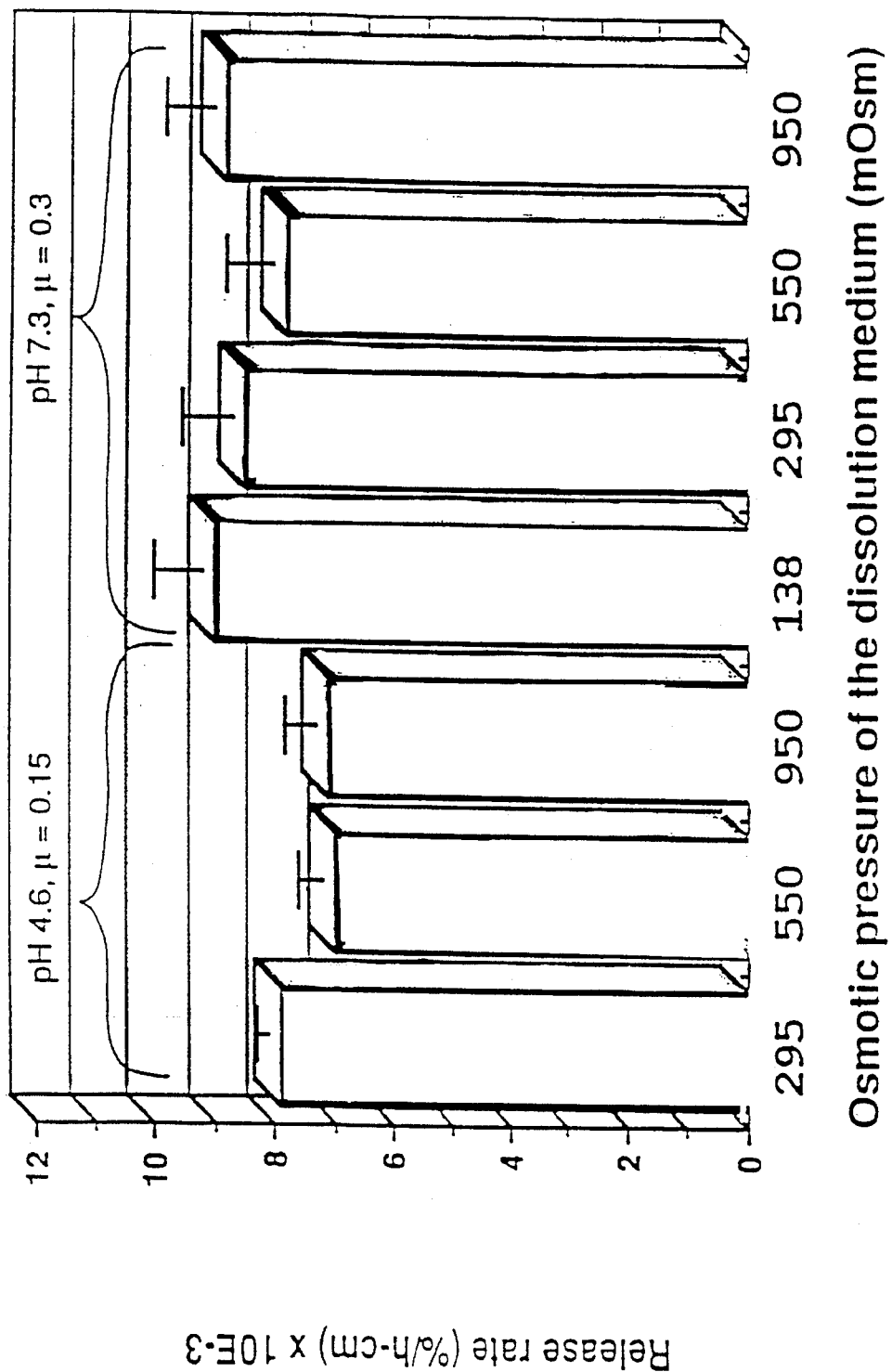
FIG. 11: Shows how the osmotic pressure of the dissolution medium affects the release rate.

The increase in the osmotic pressure of dissolution medium from 138 mOsm to 950 mOsm (pH 7.3, µ=0.3) did not affect the pH (6.8–7.8) of the device core or the amount of water absorbed in the devices during the test (7–8 µl). The influx of water into the core of the device is due to the gradient of osmotic pressure across the silicone membrane. Even at the osmotic pressure of 950 mOsm in the dissolution medium imbibition of water into the device was not prevented. The rates of propranolol release from the devices remained essentially constant (FIG. 11) as the osmotic pressure of the dissolution medium was ranged from 295 mOsm to 960 mOsm at pH=4.6 or from 138 mOsm to 950 mOsm at pH 7.4.

Figure 12:
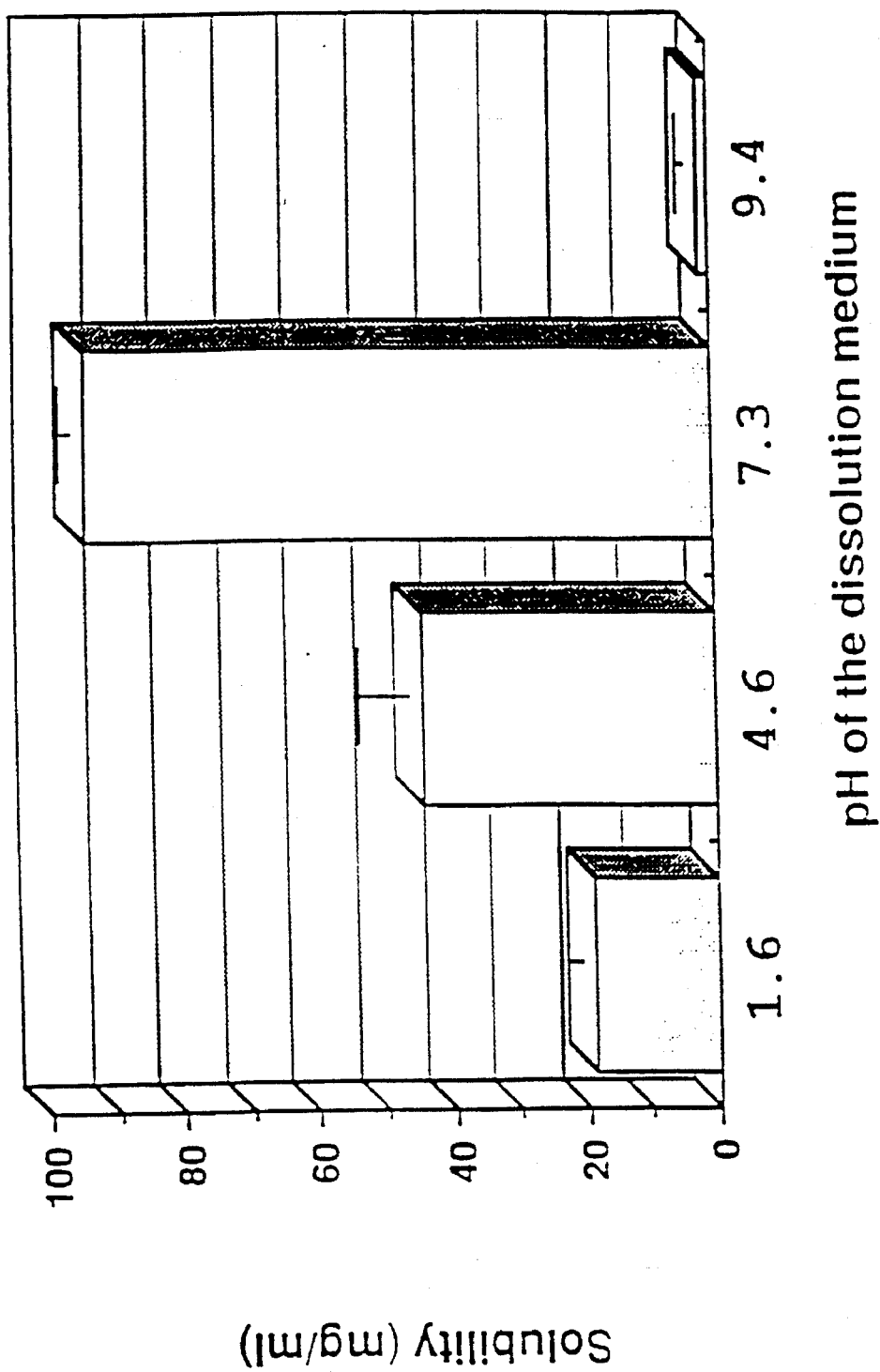
FIG. 12: Shows the solubility of propranolol hydrochloride in buffer solutions of different pH.
Figure 13:
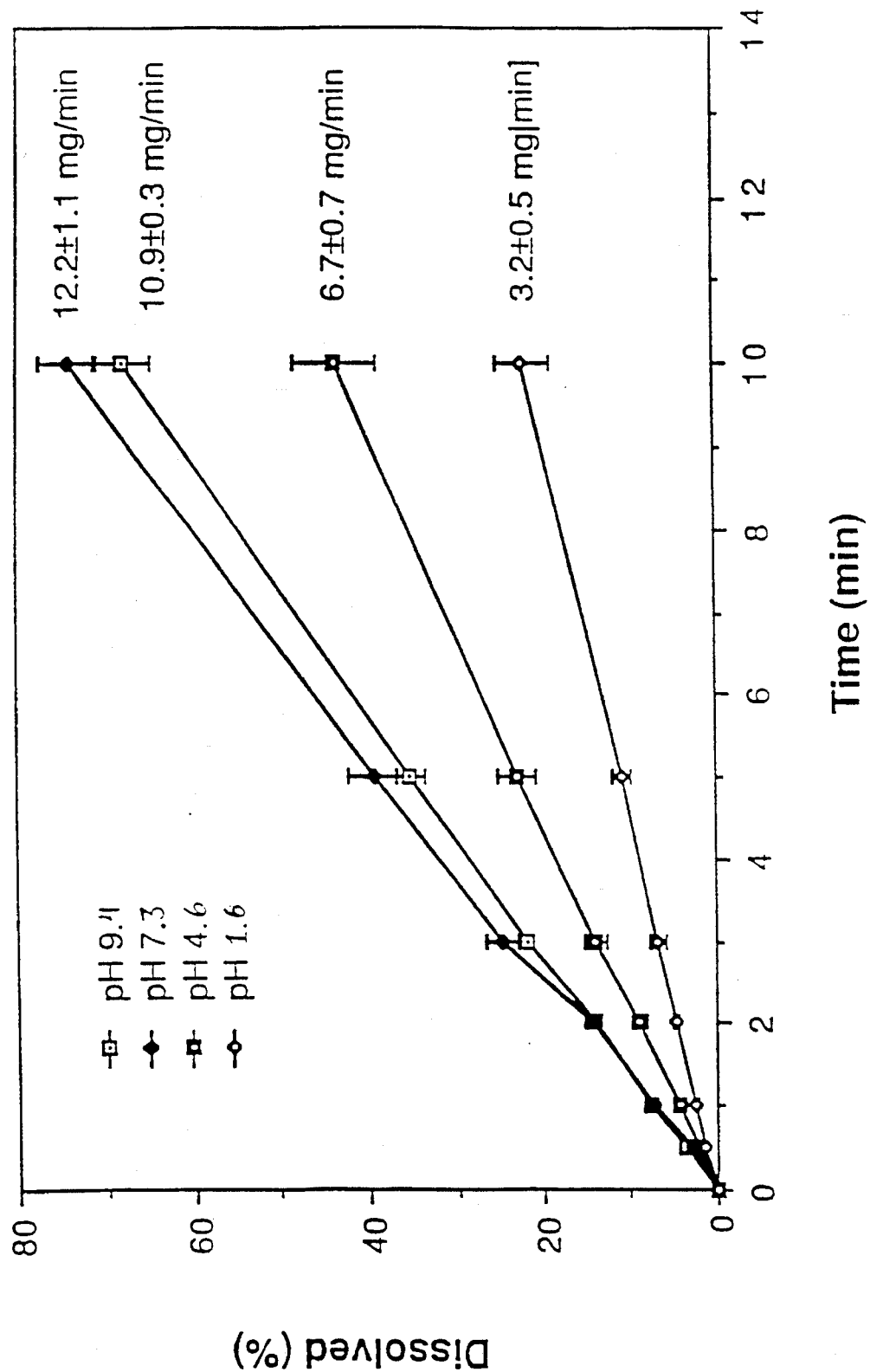
FIG. 13: Shows the dissolution rate of propranolol in solutions of different pH.

In tested buffer solutions, the solubility of propranolol hydrochloride was maximal at pH 7.3 (94 mg/ml) (FIG. 12). The dissolution rate of propranolol increased as the pH of dissolution medium was raised from 1.6 to 7.3. The rates were equal at pH 7.3 and pH 9.4 (FIG. 13).

2. Silicone Microspheres

Figure 14B:
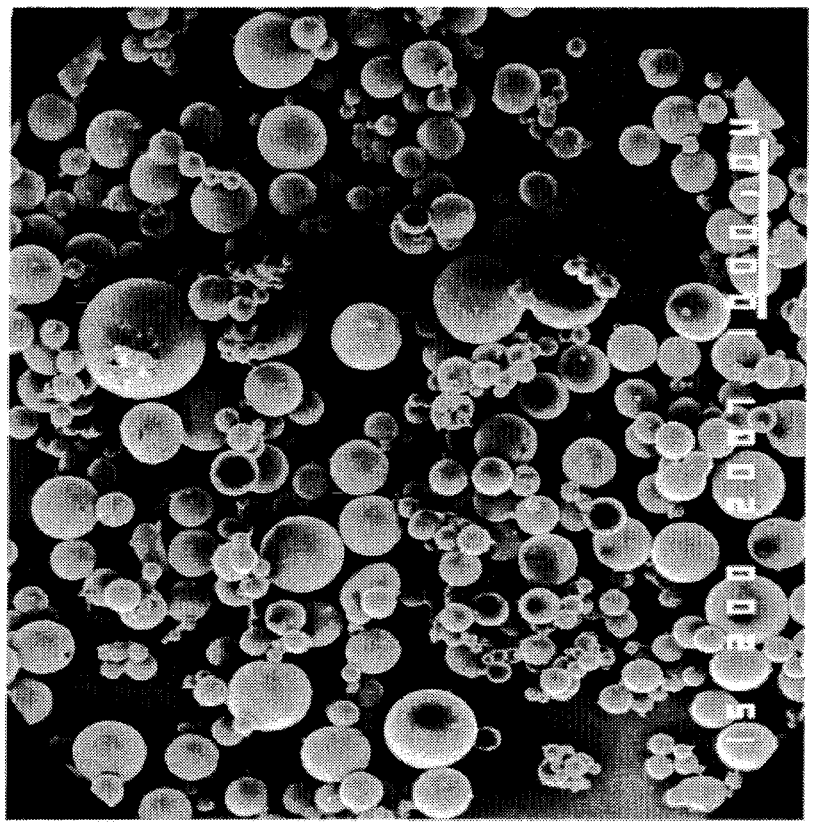
FIG. 14: Shows microspheres of timolol maleate entrapped in a silicone polymer.
Figure 14A:
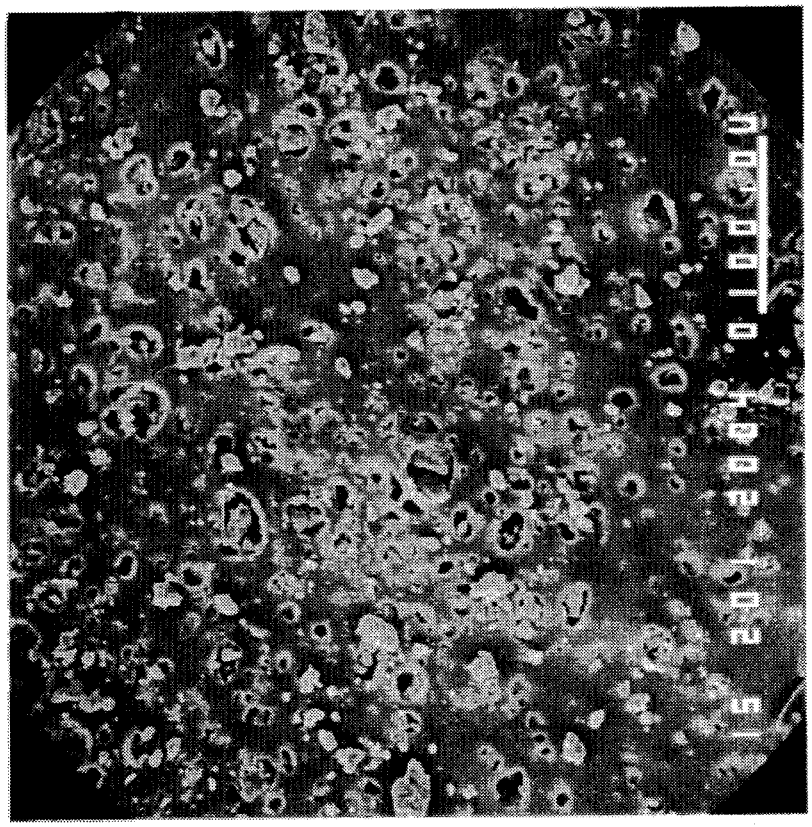

In silicone microspheres, timolol maleate was used as a model drug and sodium phosphate and Tris buffer as release-controlling adjuvants. Spray-dried drug and adjuvants were either simply mixed as power mixtures or they were spray dried together. To prepare silicone microspheres, the drug (2–20 wt %) and, if present, pH-adjusting agent (0–10 wt %) were mixed with the silicone elastomer (an amine resistant Dow Corning X7-3012 elastomer), and the curing agent was added. One part of the curing agent is mixed in ten parts of the polymer. Vulcanization of the X7-3012 elastomers is based on a platinum catalyzed addition (hydrosilylation) reaction. Two grams of the drug-polymer mixture was dispersed in 35 grams of liquid paraffin using an overhead stirrer at 190 rpm and 22° C. The temperature was raised to 50° C. in 1 hour. After 3 hours, the heating was stopped, and the mixture gradually cooled back to 22° C. Complete curing was achieved in 5 h. Microparticles were separated from paraffin by filtration, washed with n-hexane and dried at room temperature. The mean particle size of the microspheres was 150±50 µm (mean±SD) (FIG. 14) and the entrapment efficiency of timolol maleate was 60–75%. Release of timolol from the silicone microspheres was studied using the rotating bottle method (NF XIV) in pH 7.4 phosphate buffer at 37° C. The volume of dissolution medium was 3 ml and the amount of microspheres 100 mg. The release timolol was analysed using reverse phase HPLC at 294 nm.

There exists a linear relationship between the release of timolol from silicone microspheres and the square root of the time elapsed.

Figure 15:
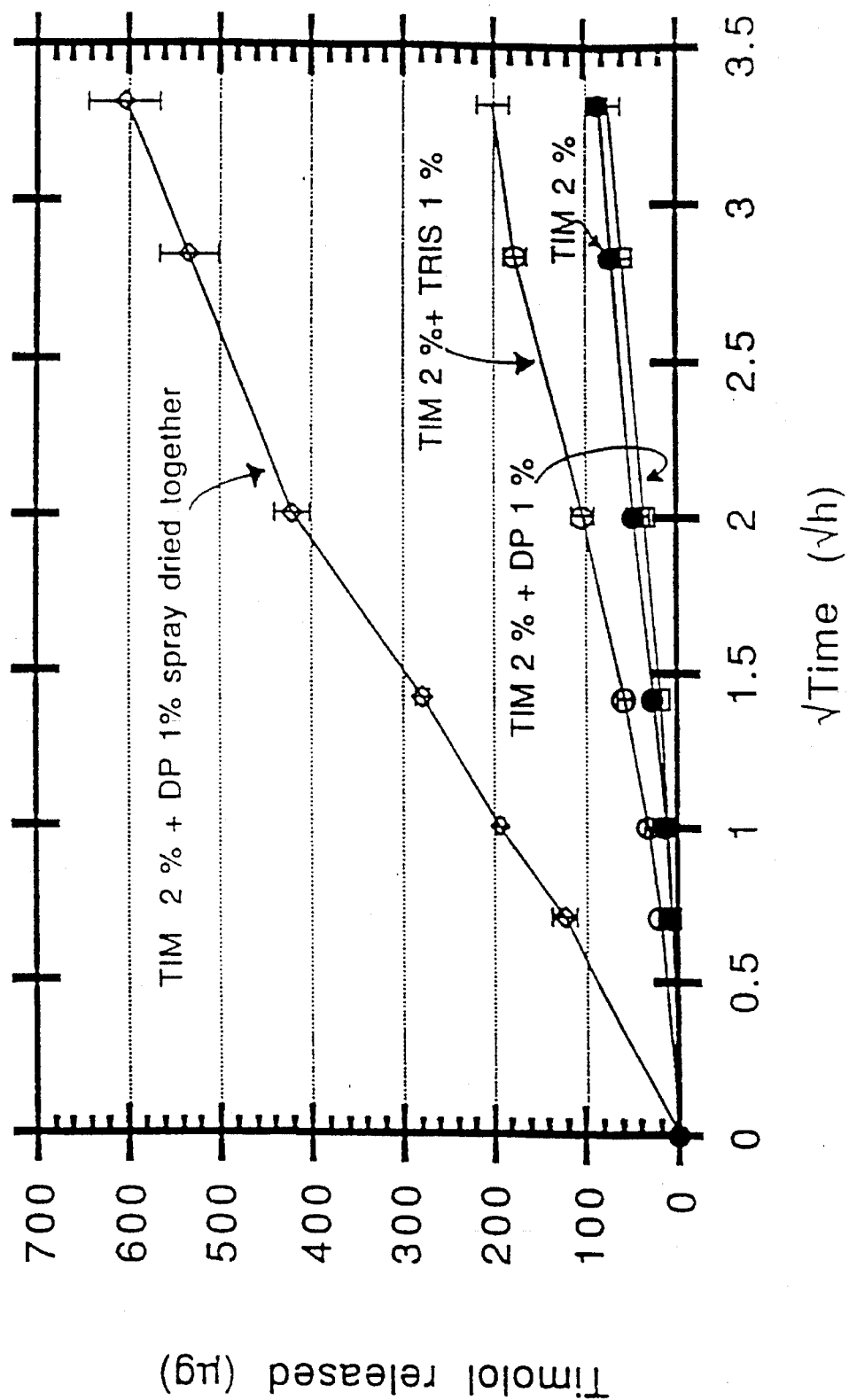
FIG. 15: Shows the release of timolol from microspheres loaded with 2 wt % timolol.
Figure 16:
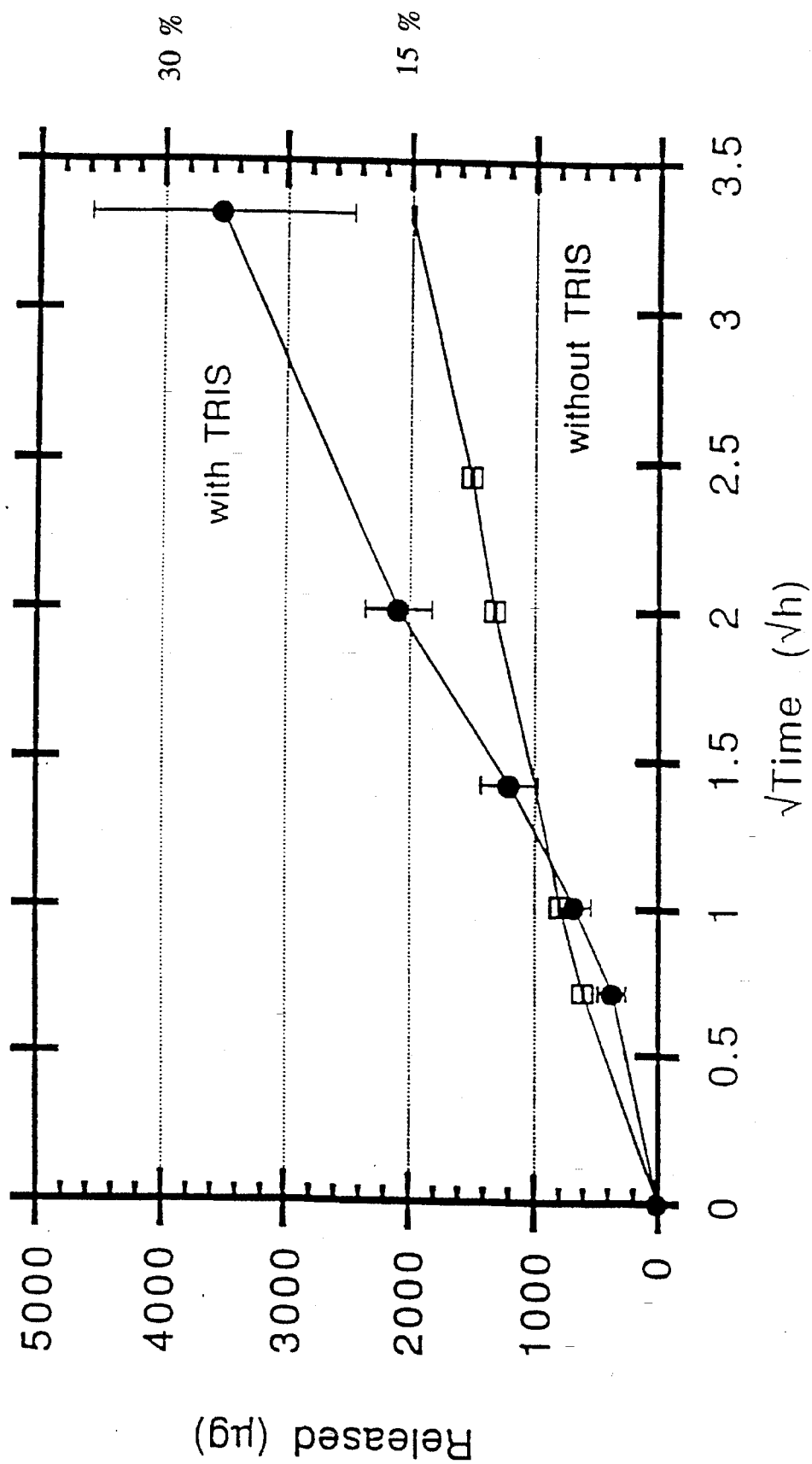
FIG. 16: Shows the release of timolol from microspheres loaded with 20 wt % timolol.

The release of timolol from silicone microspheres with drug loadings of 2 and 20 wt % were 27 and 520 µg after 1 hour, respectively (FIG. 15 and 16). Addition of 1 wt % of disodium phosphate in the microspheres containing 2 wt % of timolol did not affect the release rate (FIG. 15). When timolol and disodium phosphate were spray dried together the rate of timolol release was increased to 187 µg after 1 hour. With 1 wt % (FIG. 15) or 10 wt % of Tris (FIG. 16), timolol (2 or 20 wt %) was released two times faster than in the absence of the pH-adjusting agent.

We claim:

1. A controlled release device for peroral delivery of a therapeutic agent capable of existing in an un-ionized therapeutically active form, said device comprising a reservoir having a reservoir wall and a core containing a therapeutic agent in ionized form and a solid material that serves as a buffer upon contact with a dissolution medium wherein said reservoir wall comprises a rate-limiting elastomeric polymeric membrane to un-ionized material which is impermeable to ionized material thus preventing the penetration of ionized salts from the device core to a dissolution medium and the penetration of buffer from the dissolution medium to the device core wherein said solid material forms a pH upon contact with a dissolution medium which determines the rate of permeation of the therapeutic agent in unionized form through said reservoir wall.

2. A device according to claim 1 wherein the reservoir comprises a single macroscopic core containing the therapeutic agent and the solid material.

3. A device according to claim 1 wherein the reservoir comprises a plurality of individual cores, each core containing the therapeutic agent and the solid material.

4. A device according to claim 3 comprising microspheres or microcapsules, each microsphere or microcapsule comprising at least one core containing the therapeutic agent and the solid material.

5. A device according to claim 4 in which each microsphere or microcapsule contains a plurality of cores.

6. A device according to claim 3 wherein said membrane comprises a rate-limiting elastomeric polymeric matrix as the reservoir wall and, contained in said matrix is a plurality of individual cores each core containing said therapeutic agent and said solid material.

7. A device according to claim 1 wherein the rate-limiting elastomeric polymer is selected from the group consisting of silicones, polyisobutylene, polyhydroxyethyl methacrylate, silicone-polyethyleneoxide copolymers and styrene-butadiene copolymers.

8. A device according to claim 1 in which the reservoir wall before contacting the solid material and ionized form of the therapeutic agent has been impregnated with therapeutic agent.

9. A process for preparing a device as claimed in claim 1 comprising creating a reservoir of the therapeutic agent and solid material and placing this in contact with the reservoir wall.

10. A device according to claim 2 wherein the rate-limiting elastomeric polymer is selected from the group consisting of silicones, polyisobutylene, polyhydroxyethyl methacrylate, silicone-polyethyleneoxide copolymers and styrene-butadiene copolymers.

11. A device according to claim 3 wherein the rate-limiting elastomeric polymer is selected from the group consisting of silicones, polyisobutylene, polyhydroxyethyl methacrylate, silicone-polyethyleneoxide copolymers and styrene-butadiene copolymers.

12. A device according to claim 4 wherein the rate-limiting elastomeric polymer is selected from the group consisting of silicones, polyisobutylene, polyhydroxyethyl methacrylate, silicone-polyethyleneoxide copolymers and styrene-butadiene copolymers.

13. A device according to claim 2 in which the reservoir wall before contacting the solid material and ionized form of the therapeutic agent has been impregnated with therapeutic agent.

14. A device according to claim 3 in which the reservoir wall before contacting the solid material and ionized form of the therapeutic agent has been impregnated with therapeutic agent.

15. A process for preparing a device as claimed in claim 2 comprising creating a reservoir of the therapeutic agent and solid material and placing this in contact with the reservoir wall.

16. A process for preparing a device as claimed in claim 3 comprising creating a reservoir of the therapeutic agent and solid material and placing this in contact with the reservoir wall.

* * * * *